United States Patent [19]

Schweighardt et al.

[11] Patent Number: 4,838,274
[45] Date of Patent: Jun. 13, 1989

[54] PERFLUORO-CROWN ETHERS IN FLUORINE MAGNETIC RESONANCE IMAGING

[75] Inventors: Frank K. Schweighardt, Allentown; Joseph A. Rubertone, Coatesville, both of Pa.

[73] Assignee: Air Products and Chemicals, Inc., Allentown, Pa.

[21] Appl. No.: 99,442

[22] Filed: Sep. 18, 1987

[51] Int. Cl.$^4$ .................... A61B 6/00; A61K 49/00; G01N 24/00

[52] U.S. Cl. .................. 128/654; 128/659; 424/9; 436/173

[58] Field of Search .............. 128/654, 659, 653; 424/1.1, 4, 9; 549/352, 353; 436/68, 173; 514/450, 722

[56] References Cited

U.S. PATENT DOCUMENTS

| | | | |
|---|---|---|---|
| 4,467,351 | 8/1984 | Wang | 358/111 |
| 4,503,844 | 3/1985 | Siczek | 128/71 |
| 4,523,039 | 6/1985 | Lagow et al. | 568/615 |
| 4,543,959 | 10/1985 | Sepponen | 128/653 |
| 4,544,545 | 10/1985 | Ryan et al. | 424/1.1 |
| 4,558,279 | 12/1985 | Ackerman et al. | 324/315 |
| 4,561,001 | 12/1985 | Gunn et al. | 346/218 |
| 4,570,004 | 2/1986 | Lagow et al. | 549/352 |
| 4,573,014 | 2/1986 | Riederer | 324/307 |
| 4,577,636 | 3/1986 | Spears | 128/654 |
| 4,586,511 | 5/1986 | Clark, Jr. | 128/653 |
| 4,587,493 | 5/1986 | Sepponen | 324/319 |
| 4,598,368 | 7/1986 | Umemura | 364/414 |
| 4,604,743 | 8/1986 | Alexandru | 370/85 |
| 4,612,185 | 9/1987 | Dean | 424/2 |
| 4,626,784 | 12/1986 | Sepponen | 324/309 |
| 4,631,495 | 12/1986 | Mueller et al. | 330/310 |
| 4,639,364 | 1/1987 | Hoey | 424/9 |
| 4,647,447 | 3/1987 | Gries et al. | 424/9 |
| 4,651,098 | 3/1987 | Yamada et al. | 324/309 |
| 4,652,643 | 3/1987 | Gunn et al. | 544/37 |
| 4,654,593 | 3/1987 | Ackerman | 324/307 |

FOREIGN PATENT DOCUMENTS

| | | | |
|---|---|---|---|
| 0118281 | 9/1984 | European Pat. Off. | 24/8 |
| 2109407 | 6/1983 | United Kingdom | 436/548 |

OTHER PUBLICATIONS

Wen-Huey Lin et al., J. Chem. Soc., Chem. Commun., 1985, pp. 1350-1352, "The First Perfluro Crown Ethers".

Lauterbur, Nature, 242, 190-191, 1973-"Image Formation by Induced Local Interactions: Examples Employing Nuclear Magnetic Resonance".

Damadian, Science, 171, 1151, 1971-"Tumor Detection by Nuclear Magnetic Resonance".

Robert F. Mattrey, SPIE, vol. 626, Medicine, XIV/-PACS IV (1986), pp. 18-23, "Perfluorocarbon Compounds: Applications in Diagnostic Imaging".

Mattrey et al., "Perfluorochemicals as U.S. Contrast Agents for Tumor Imaging and Hepatosplenography: Preliminary Clinical Results", Radiology, vol. 163, No. 2, pp. 339-344.

N. J. Patronas, J. Hekmatpanah, Kunio Doi, "Brain-Tumor Imaging using Radiopaque Perfluorocarbon", J. Neurosurg./vol. 58, May, 1983, pp. 650-653.

Longmaid et al., "In Vivo 19F NMR Imaging", Investigative Radiology, Mar.-Apr. 1985, vol. 20.

Reid et al., "The Influence of Oxygenation on the 19F Relaxation Rates in Fluosol-DA Blood Substitute".

Wyrwicz et al., "In Vivo 19F NMR Study of Fluorinated Anesthetics Elimination from a Rabbit Brain".

Thomas et al., "NMR Imaging of the Lung Using Liquid Perfluorocarbon".

Koutcher et al., "In Vivo Imaging and Spectroscopy of Fluorinated Blood Substitutes".

Horner et al., "Evaluation of Myocardial Perfusion by 19F NMR Imaging".

*Primary Examiner*—C. Fred Rosenbaum
*Assistant Examiner*—Sharon Rose
*Attorney, Agent, or Firm*—Geoffrey L. Chase; William F. Marsh; James C. Simmons

[57] ABSTRACT

A method is disclosed for nuclear magnetic resonance imaging wherein the improvement is the use of perfluoro 15-crown-5 ether which has 20 magnetically similar fluorine atoms providing a superior signal to noise ratio with resultant enhanced diagnostic resolution.

8 Claims, No Drawings

PERFLUORO-CROWN ETHERS IN FLUORINE MAGNETIC RESONANCE IMAGING

TECHNICAL FIELD

The present invention is directed to magnetic resonance imaging, also referred to as nuclear magnetic resonance imaging. More particularly, the present invention is directed to methods and compositions for improving magnetic resonance images of body organs and tissues using fluorochemicals having unexpectedly enhanced signal to noise response ratios.

BACKGROUND OF THE PRIOR ART

The recently developed techniques of MRI (magnetic resonance imaging) or NMR (nuclear magnetic resonance) imaging encompasses the detection of certain atomic nuclei utilizig magnetic fields and radio-frequency radiation. It is similar in some respect to X-ray computed tomography (CT) in providing a cross-sectional display of the body organ anatomy with excellent resolution of soft tissue detail. In current use, the images produced constitute a map of the distribution density of protons and/or their relaxation times in organs and tissues. The MRI technique is advantageously non-invasive as it avoids the use of ionizing radiation.

While the phenomenon of NMR was discovered in 1945, it is only relatively recently that it has found application as a means of mapping the internal structure of the body as a result of the original suggestion of Lauterbur (Nature, 242, 190-191, 1973). The lack of any known hazard associated with the level of the magnetic and radio-frequency fields that are employed renders it possible to make repeated scans on vulnerable individuals. Additionally, any scan plane can readily be selected including transverse, coronal, and sagittal sections.

In an NMR experiment, the nuclei under study in a sample (e.g. protons) are irradiated with the appropriate radio-frequency (RF) energy in a highly uniform magnetic field. These nuclei, as they relax, subsequently emit RF radiation at a sharp resonant frequency. The emitted frequency (RF) of the nuclei depends on the applied magnetic field.

According to known principles, nuclei with appropriate spin when placed in an applied magnetic field [B, expressed generally in units of gauss or tesla ($10<4>$-gauss)] align in the direction of the field. In the case of protons, these nuclei precess at a frequency $f=42.6$ MHz at a field strength of 1 Tesla. At this frequency, an RF pulse of radiation will excite the nuclei and can be considered to tip the nuclei out of the field direction, the extent of this rotation being determined by the pulse duration and energy. After the RF pulse, the nuclei "relax" or return to equilibrium with the magnetic field, emitting radiation at the resonant frequency. The decay of the signal is characterized by two relaxation times, i.e., T1, the spin-lattice relaxation time or longitudinal relaxation time, that is, time taken by the nuclei to return to equilibrium along the direction of the externally applied magnetic field, and T2, the spin-spin relaxation time associated with the dephasing of the initially coherent precession of individual proton spins. These relaxation times have been established for various fluids, organs and tissues in different species of mammals.

In MRI, scanning planes and slice thickness can be selected without loss of resolution. This permits high quality transverse, coronal and sagittal images to be obtained directly. The absence of any moving parts in MRI equipment promotes a high reliability. It is believed that MRI or NMR imaging has a greater potential than CT for the selective examination of tissue characteristics in view of the fact that in CT, X-ray attenuation coefficients alone determine image contrast, whereas at least four separate variables (T1, T2, nuclear spin density and flow) may contribute to the NMR signal. For example, it has been show (Damadian, Science, Vol. 171, p. 1151, 1971) that the values of the T1 and T2 relaxation in tissues are generally longer by about a factor of 2 in excised specimens of neoplastic tissue compared with the host tissue.

By reason of its sensitivity to subtle physio-chemical differences between organs and/or tissues, it is believed that MRI may be capable of differentiating tissue types and in detecting diseases which induce physio-chemical changes that may not be detected by X-ray or CT which are only sensitive to differences in the electron density of tissue. The images obtainable by MRI techniques also enable the physician to detect structures smaller than those detectable by CT and thereby provide comparable or better spatial resolution.

The use of perfluorocarbon compounds in various diagnostic imaging technologies such as ultrasound, magnetic resonance, radiography and computed tomography, has been set forth in an article by Robert F. Mattrey in SPIE, Volume 626, Medicine, XIV/PACS IV (1986), pages 18-23.

Magnetic resonance imaging of liver tumor in rats using perfluorochemical emulsions was reported in "In Vivo $^{19}F$ NMR Imaging of Liver, Tumor and Abcess in Rats", H. E. Longmaid III, et al., INVESTIGATIVE RADIOLOGY, March-April 1985, Vol. 20, p. 141-144. The compounds utilized displayed multiple peak NMR spectra.

Imaging of brain tumors with perfluorooctyl bromide has been described in "Brain-Tumor Imaging Using Radiopaque Perfluorocarbon", Nicholas J. Patronas, M.D., et al. JOURNAL OF NEUROSURGERY, May 1983, Vol. 58, pp. 650-653.

Ultrasound imaging of organs has been enhanced by FLUOSOL-DA (perfluorodecalin and perfluorotripropylamine) as reported in "Perfluorochemicals as US Contrast Agents for Tumor Imaging and Hepatosplenography: Preliminary Clinical Results", Robert F. Mattrey, M.D., et al., RADIOLOGY, May 1987, Vol. 163, No. 2, pp. 339-343.

In European published Patent Application 0 118 281, published September 12, 1984, a technique for the detection of gas in an animal is set forth using nuclear magnetic resonance techniques embodying various fluorochemical agents. Among the fluorochemical agents there is included perfluoroether polymer (Fomblin Y/01).

In U.S. Pat. No. 4,523,039 the production of fluorocarbon ethers of various structures is set forth wherein the resulting fluorocarbon ether produces a noncyclic structure.

U.S. Pat. No. 4,570,004 describes a method of production and a composition of matter including perfluoro 15-crown-5 ether. The patent identifies that the crown ethers in general can be useful as oxygen carriers and various biomedical products.

U.S. Pat. No. 4,639,364 discloses the use of various fluorine-containing compounds for magnetic resonance imaging.

The prior art, despite its suggestion for the use of magnetic resonance imaging for medical and biodiagnostic purposes and the prior art's suggestion of various fluorine-containing compounds for use as agents in nuclear magnetic resonance imaging, has failed to provide a particularly sensitive fluorine agent for nuclear magnetic resonance imaging which provides high signal to noise ratios sufficient for detailed diagnosis of deep tissue structures and fine resolution requirements.

BRIEF SUMMARY OF THE INVENTION

The present invention is directed to a method for obtaining fluorine magnetic resonance images of body organs or tissues by administering to a mammal a fluorine-containing agent in a sufficient amount to provide fluorine magnetic resonance images of said organs or tissues and imaging said organs and tissues wherein the improvement comprises using as said fluorine-containing agent perfluoro 15-crown-5 ether.

Preferably, the perfluoro 15-crown-5 ether is administered in an aqueous isotonic emulsion with a fluorochemical concentration range of 5 to 25 wt%.

A particular embodiment of the present invention constitutes administering the perfluoro 15-crown-5 ether in emulsion form to the cerebrospinal fluid compartment of a mammal for imaging of the cerebrospinal structures for diagnostic purposes.

The perfluoro 15-crown-5 ether emulsion may be administered by a technique of direct injection into a body part, a body compartment, the bloodstream or by inhalation.

Alternativly, a method of the present invention can be performed by administering the perfluoro 15-crown-5 ether to a mammal, performing a biopsy of selected organ or body tissue and imaging the biopsied tissue in vitro.

DETAILED DESCRIPTION OF THE INVENTION

Fluorine atoms $^{19}F$ give a clear nuclear magnetic resonance signal and thus may function as suitable probes in nuclear magnetic resonance imaging when combined in a chemically suitable form. The specific advantages flowing from the use of $^{19}F$ are:
(1) its low intrinsic concentration in soft tissues of the body;
(2) its high nuclear magnetic resonance sensitivity, and
(3) a magnetogyric ratio which is close to that of hydrogen, thereby making the observation of $^{19}F$ compatible with existing imaging devices.

However, the mere use of $^{19}F$ in various compounds does not provide the unexpected enhancement achieved by the present invention wherein the use of perfluoro 15-crown-5 ether provides the multiplied effect of 20 identically electronically and/or magnetically situated fluorine atoms. This particular chemical structure of fluorines provides a uniquely sharp signal when using nuclear magnetic resonance imaging in a biocompatible fluorine-containing agent. Perfluoro crown ethers have generally been recognized as having utility in biomedical applications. However, the present inventor has found that perfluoro 12-crown-4 ether is too volatile to be placed in the bloodstream of a mammal because of its tendency to form embolisms. On the other hand, perfluoro 18-crown-6 ether is to heavy in molecular weight for biomedical application, and despite its emulsification in a reasonably stable emulsion, when the agent is administered to a mammal, the ether precipitates out as a solid and shows marked toxicity.

Unexpectedly, perfluoro 15-crown-5 ether does not form embolisms and does not precipitate out of emulsion when administered to a mammal in an effective concentration sufficient for unexpectedly high signal to noise response ratios in magneic resonance imaging, particularly for cisternography which is a diagnostic technique for the determination of open spaces in organs, particularly the spaces surrounding and involved in brain tissue.

The unique location and association of fluorine atoms in perfluoro crown ethers provides the single sharp resonance line of maximum signal to noise ratio when used in magnetic rsonance imaging, because of the magnetic equivalence of all fluorine nuclei. The provides the unique non-intrusive diagnostic capabilities of perfluoro crown ethers fills the need for a cerebrospinal diagnostic technique that does not involve radionucleid introduction or X-ray detection or without the administration of a contrast enhancement agent, wherein the present method provides reduced neurotoxicity compared to present technology.

The present invention can be practiced by preparing a suitable perfluoro-15-crown-5 ether microemulsion in a biocompatible isotonic aqueous phase for injection into the cerebrospinal fluid (CSF) compartment. This compartment consists of the right and left lateral ventricles, the intraventricular foramina of Monroe, the third ventricle, the cerebral aqueduct of Sylvius, the fourth ventricle, the midline foramen of Magendie, the lateral toramina of Luschka, the cerebral subarachnoid space and its associted cisterns (cerebellomedullary [magna or ambiens], superior, lamina terminalis, chiasmatic, interpeduncular and pontine), the spinal subarachnoid space and the lumbar cistern. CSF is produced by the choroid plexi of the lateral and fourth ventricles. This fluid, derived from the choroidal arteries, is believed to be a secretory product involving active transport mechanism. CSF flows from the laterial ventricles, through the foramina of Monroe, to the third ventricle. The cerebral aqueduct then carries the fluid back to the fourth ventricle where it exits to the cerebellomedullary cistern via the foramina of Magendie and Luschka. The CSF then flows from this site and circulates through the subarachnoid spaces and associated cisterns of the brain and spinal cord. This fluid is then passively returned to the venous system via the arachnoid villi. The rate of CSF formation in man is estimated to be between 600 and 700 ml per day. Since the total volume of the subarachnoid space and ventricles in man is about 140 ml the daily flow rate is appreciable. The perfluoro-15-crown-5 ether emulsion preparation can be neurostereotactically injected into either the lateral ventricle, the cerebellomedullary cistern or the lumbar cistern of the spinal subarachnoid space. Approximately one hour post-injection a $^{19}F$ magnetic resonance image can be taken of the head and neck region or spinal region of the administered mammal. The resulting magnetic resonance image is specific for the fluorine nuclei and provides a unique map of the cerebrospinal fluid compartment in question. Images following injection of the lateral ventricle depict the space of the lateral ventricle, foramina of Monroe, third ventricle, cerebral aqueduct, and fourth ventricle. Injections of the cerebellomedullary and lumbar cistern allow for images of the cerebral and spinal subarachnoid spaces respectively.

Accordingly, the perfluoro-15-crown-5 ether emulsion can be administered by direct injection into a body part, direct injection into a body cavity (thoracic, peritoneal), direct injection into a body compartment (CSF), direct injection into a space (subarachnoid), direct injection into a joint capsule, direct injection into the blood stream or by inhalation.

Despite the particular application to cerebrospinal diagnostic, the perfluoro crown either of the present invention may also be utilized to measure oxygen concentration in vivo of mammals, wherein the perfluoro crown ether in emulsion form, is administered to the vascular system of the mammal.

The perfluoro 15-crown-5 ether emulsion form is thought to be useful for nuclear magnetic resonance diagnostic imaging to enhance the contrast between the cerebrospinal fluid, the brain and the spinal cord for diagnosis of tumors adjacent to the cerebrospinal fluid compartment, arachnoic cysts, cerebrospinal fluid rhinorrhea and otorrhea, papillomas, pinealomas, arachnoiditis and internal hydrocephaly. The perfluoro 15-crown-5 ether is capable of highlighting specific biological dysfunctions as set forth above. Additional diagnostic areas of interest include cardiovascular blood transport, which can be observed for site blockage, gastrointestinal constrictions which could be outlined, lung capacity and tissue degeneration could be located and tumor detection could be determined during early stages of tumor development due to the heightened sensitivity of the specific perfluoro crown ether.

Perfluoro 15-crown-5 ether was the only member of the perfluoro crown ether class of materials identified in U.S. Pat. No. 4,570,004 (hereby incorporated herein by reference) to form a stable aqueous emulsion at concentrations of 5 to 25 wt% in sterile saline with nonionic surfactant systems and also provide biocompatibility. This perfluoro crown ether was formulated into an approrpiate emulsion as set forth in the following example.

EXAMPLE 1

An emulsion of perfluoro 15-crown-5 ether was prepared in sterile saline. One gram of perfluoro 15-crown-5 ether was sonicated for 5 minutes at 20° C. with 0.27 grams supercritically extracted egg yolk lecithin in 4.5 grams of normal saline.

EXAMPLE 2

In a typical control experiment, a normal, female Sprague-Dawley rat weighing approximately 290 grams, was anesthetized with ketamine hydrochloride. It was then injected directly into the fourth ventricle with five (5) microliter aliquots of the PF15C-5E emulsion (18 wt% fluorochemical) every five minutes until fifty microliters was injected. The animal was then isolated. The animal appeared normal and allowed to survive for 30 days. Gross examination did not reveal any irregularity. It was concluded that the fluorochemical emulsion was not toxic to the CNS (Central Nervous System).

EXAMPLE 3

In a typical experiment, a normal female Wistar rat weighing approximately 300 grams was anesthetized with ketamine hydrochloride. After sedation, the animal was injected into the fourth ventricle with five microliters of the PF15C-5E emulsion (18 wt% fluorochemical) every five minutes until fifty microliters had been injected. After one hour and forty-five minutes an additional 0.13cc of ketamine was injected to maintain a constant level of sedation during $^{19}F$ NMR imaging.

The $^{19}F$ imaging was conducted on a 1.4 Kgauss superconducting solenoid over a period of one and one-half hours with a pulse rate of 130 msecs. The final image was processed at $128 \times 128$ pixel resolution. The spectrometer was reconfigured for $^{19}F$ spectroscopy and a high resolution $^{19}F$ spectrum was taken to confirm a single sharp line resonance signal.

The present invention has been set forth with emphasis of a particular preferred embodiment. However, the scope of the present invention should be ascertained from the claims which follow.

We claim:

1. In a method for obtaining fluorine magnetic resonance images of body organs or tissues by adminstering to a mammal a fluorine-containing agent in a sufficient amount to provide fluorine magnetic resonance images of said organs or tissues and imaging said organs and tissues, the improvement comprising using as said fluorine-agent an aqueous isotonic emulsion of perfluoro 15-crown-5 ether.

2. The method of claim 1 wherein the concentration of the emulsion is in the range of 5 to 25 wt% of the perfluoro 15-crown-5 ether.

3. The method of claim 1 wherein said fluorine-containing agent is administered to the cerebrospinal fluid compartment of a mammal.

4. The method of claim 1 wherein the fluorine-containing agent is administed by a process selected from the group consisting of direct injection into a body part, direct injection into a body cavity (thoracic, peritoneal), direct injection into a body compartent (CSF), direct injection into a space (subarachnoid), direct injection into a joint capsule, direct injection into the bloodstream or inhalation.

5. The method of claim 1 wherein after administration of the agent to the mammal, the desired tissue is biopsied and the biopsied and extracted tissue is imaged.

6. The method of claim 1 wherein the imaging is spinal cisternography.

7. The method of claim 1 wherein the imaging is cerebral cisternography.

8. A method of cisternography for obtaining fluorine magnetic resonance images of cerebrospinal structures of brain tissues by direct injection into a mammalian cerebrospinal fluid compartment of an aqueous biocompatible isotonic emulsion of perfluoro 15-crown-5 ether in a sufficient amount to provide fluorine magnetic resonance images of said cerebrospinal structures and imaging said cerebrospinal structures.

* * * * *

UNITED STATES PATENT AND TRADEMARK OFFICE
CERTIFICATE OF CORRECTION

PATENT NO.  : 4,838,274

DATED       : June 13, 1989

INVENTOR(S) : Schweighardt, et al

It is certified that error appears in the above-identified patent and that said Letters Patent is hereby corrected as shown below:

Column 6, line 29 and 30
   After "fluorine-", add --containing--

Signed and Sealed this

Twenty-seventh Day of November, 1990

Attest:

HARRY F. MANBECK, JR.

Attesting Officer

Commissioner of Patents and Trademarks